(12) United States Patent
Ganser et al.

(10) Patent No.: US 6,907,798 B2
(45) Date of Patent: Jun. 21, 2005

(54) DEVICE FOR LASER CUTTING PREPARATIONS, AND A MICROSCOPE

(75) Inventors: Michael Ganser, Giessen (DE); Albrecht Weiss, Linden (DE); Ruediger Stenzel, Hilchenbach (DE)

(73) Assignee: Leica Microsystems Wetzlar GmbH, Wetzlar (DE)

( * ) Notice: Subject to any disclaimer, the term of this patent is extended or adjusted under 35 U.S.C. 154(b) by 162 days.

(21) Appl. No.: 10/257,153

(22) PCT Filed: Mar. 21, 2001

(86) PCT No.: PCT/DE01/01082
§ 371 (c)(1),
(2), (4) Date: Oct. 9, 2002

(87) PCT Pub. No.: WO01/79911
PCT Pub. Date: Oct. 25, 2001

(65) Prior Publication Data
US 2003/0075530 A1 Apr. 24, 2003

(30) Foreign Application Priority Data
Apr. 13, 2000 (DE) .......................................... 100 18 251

(51) Int. Cl.$^7$ ................................................. G01N 1/04
(52) U.S. Cl. ................................................. 73/864.41
(58) Field of Search ......................... 73/864.41, 864.59

(56) References Cited

U.S. PATENT DOCUMENTS

| 5,337,178 A | | 8/1994 | Kung et al. |
| 5,523,941 A | * | 6/1996 | Burton et al. .................. 700/60 |
| 5,587,833 A | * | 12/1996 | Kamentsky .................. 359/393 |
| 5,691,841 A | * | 11/1997 | Ohsaki et al. ............... 359/391 |
| 5,843,644 A | | 12/1998 | Liotta et al. |
| 5,998,129 A | | 12/1999 | Schütze et al. |

FOREIGN PATENT DOCUMENTS

| DE | 245 501 A1 | 5/1987 |
| DE | 91 10 075.5 U1 | 1/1992 |
| DE | 43 00 698 A1 | 7/1994 |

(Continued)

OTHER PUBLICATIONS

Schütze et al., "Identification of expressed genes by laser–mediated manipulation of single cells," *Nature Biotechnology* (Aug. 16, 1998), vol. 16, pp. 737–742, XP000999459, ISSN: 1087–0156.

Isenberg et al., "Cell surgery by laser micro–dissection: a preparative method," *Journal of Microscopy* (May 1, 1976); vol. 107, No. 1, pp. 19–24, XP000671562, ISSN: 022–2720.

R. Bonner et al., "Laser Capture Microdissection: Molecular Analysis of Tissue," Science, vol. 278, Nov. 1997, pp. 1481 and 1483.

P.A.L.M. Mikrolaser Technologie, "Catch and Move —Cut or Fuse, PALM Laser–Microbeam Systems for Non–Contact and Precise Micromanipulations".

*Primary Examiner*—Hezron Williams
*Assistant Examiner*—Rodney T. Frank
(74) *Attorney, Agent, or Firm*—Foley & Lardner LLP

(57) ABSTRACT

The invention relates to a device for laser cutting preparations which comprises an XY table (2) that defines a table surface (4). A holding device (14) for accommodating an object support (6) with a preparation (8) is arranged above the table surface (4) and is joined to the XY table (2) in a manner that permits it to be displaced in the Y direction (20a) in the X direction (22a). An open working space (16) is defined between the holding device (14) and the table surface (4). A catching device (10), which has at least one receptacle (12) for catching a preparation part that has been cut out, can be introduced into said working space. The invention also relates to a microscope that is equipped with the aforementioned laser cutting device.

10 Claims, 3 Drawing Sheets

FOREIGN PATENT DOCUMENTS

Figure 1:
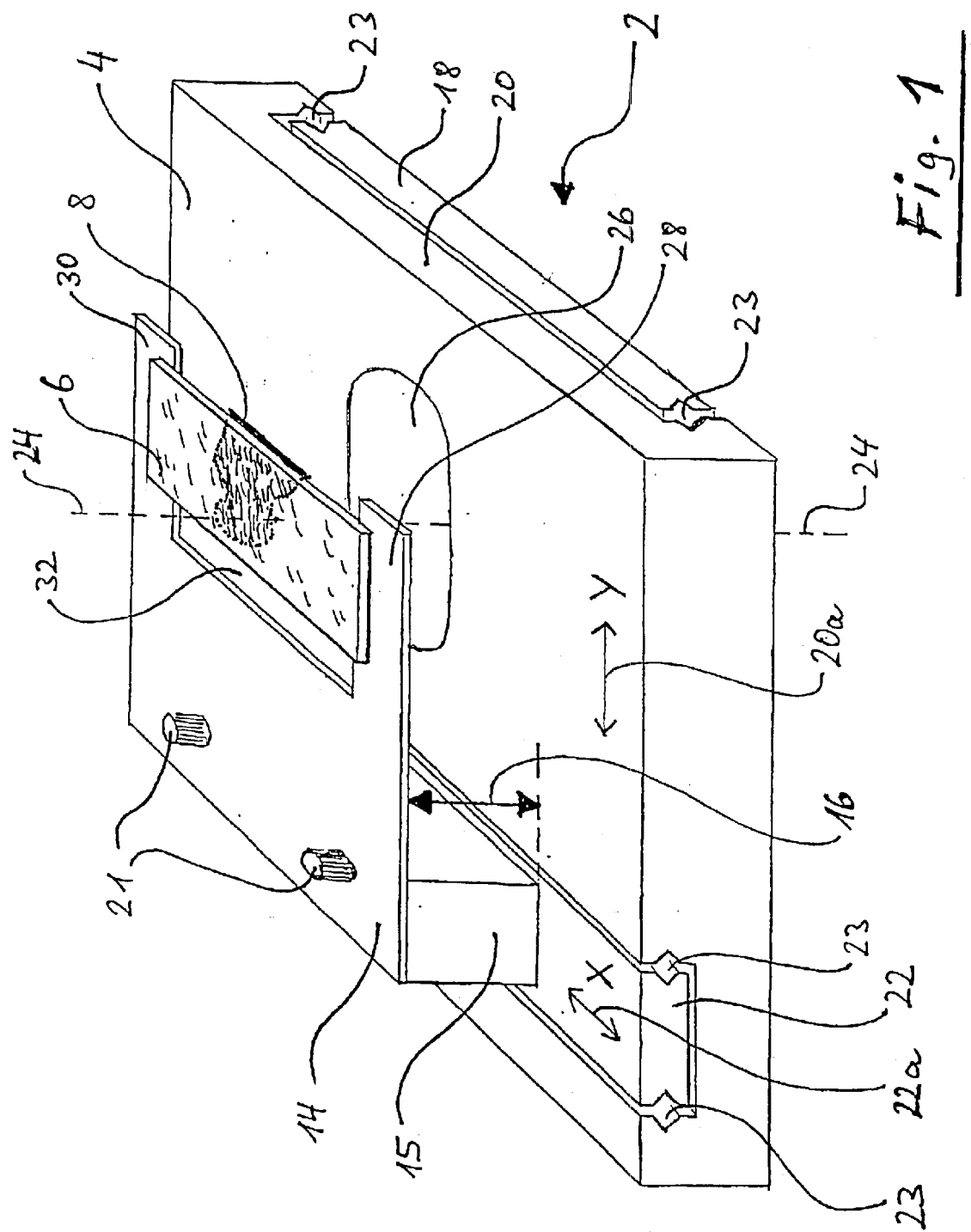

| | | |
|---|---|---|
| DE | 196 03 996 A1 | 8/1997 |
| DE | 196 16 216 A1 | 10/1997 |
| DE | 297 23 120 | 6/1998 |
| EP | 0 679 325 B1 | 11/1995 |
| WO | 94/16543 A1 | 7/1994 |
| WO | 95/23960 A1 | 9/1995 |
| WO | 97/13838 A1 | 4/1997 |
| WO | 97/29354 A1 | 8/1997 |
| WO | 97/29355 A1 | 8/1997 |
| WO | 98/35215 A1 | 8/1998 |
| WO | 98/35216 A1 | 8/1998 |
| WO | WO 98/35216 A1 | 8/1998 |
| WO | 98/36261 A1 | 8/1998 |
| WO | 99/00658 A1 | 1/1999 |
| WO | 99/17094 A2 | 4/1999 |

* cited by examiner though the drive motors make access to the region underneath the preparation more difficult. In particular, collecting devices comprising arrays of individual containers cannot be used in most cases.

DEVICE FOR LASER CUTTING PREPARATIONS, AND A MICROSCOPE

The invention relates to a device for laser cutting preparations. In particular, the invention comprises an xy table which defines a table surface, comprising a holder to hold an object carrier the object carrier, being seated in the holder in such a way that the preparation is opposite the table surface and a collecting device having at least one container to collect a part of the preparation cut out.

Furthermore, the invention relates to a microscope which is used together with the device for laser cutting preparations. The microscope comprises an xy table which defines a table surface, comprising a holder to hold an object carrier, the object carrier being seated in the holder in such a way that the preparation is opposite the table surface and a collecting device having at least one container to collect a part of the preparation cut out.

DE 196 16 216 A1 describes a method and a device for the laser dissection of biological objects. It comprises a microscope arrangement for viewing thin layers of the objects on an object carrier, the object carrier resting on a holder integrated into the xy table and the thin layer being located on the underside of the object carrier. A laser arrangement produces a focussed laser beam to cut sample material out of the thin layers. The laser arrangement and the object carrier can be displaced relative to each other. Arranged underneath the xy table is a collecting device to hold the sample material cut out. The collecting device comprises one or more containers.

The drawback with the arrangement described is that the collecting device has to be introduced from below into the table cutout in the region underneath the preparation. This region is difficult for the user to see or to reach. This region is particularly difficult to access in xy tables which are constructed as three-plate tables and therefore have a high overall shape. In addition, the region is difficult to access in motor-operated xy tables, since the drive motors make access to the region underneath the preparation more difficult. In particular, collecting devices comprising arrays of individual containers cannot be used in most cases.

On the basis of this prior art, the invention is based on the object of configuring a device for laser cutting microscopic preparations in such a way that the handling of a collecting device for holding the part of the preparation cut out can be carried out safely, simply and conveniently. Furthermore, the contamination of the containers of the collecting device with particles liberated during the cutting is to be reduced to a minimum.

This object is achieved by a device for laser cutting preparations comprising an xy table (2) which defines a table surface (4), a holder (14) to hold an object carrier (6), the object carrier (6) being seated in the holder (14) in such a way that the preparation (8) is opposite the table surface (4)

and a collecting device (10) having at least one container (12) to collect a part of the preparation cut out, which is characterized in that the holder (14) is arranged above the table surface (4) and is connected to the xy table (2) in such a way that it can be displaced in the y direction (20a) and in the x direction (22a), and in that, between the holder (14) and the table surface (4), a free working space (16) is defined, into which the collecting device (10) can be fed.

It is a further object of the invention to provide a microscope with which parts of the preparation can be cut out of a preparation by a laser, safe and simple transfer into collecting containers being ensured.

This object is achieved by a microscope which is characterized in that the holder (14) is arranged above the table surface (4) and is connected to the xy table (2) in such a way that it can be displaced in the x direction (22a) and in the y direction (20a), and in that between the holder (14) and the table surface (4), a free working space (16) is defined, into which the collecting device (10) can be fed.

It is particularly advantageous in the invention that safe and easily handled holding of the parts of the preparation cut out in containers provided for the purpose and belonging to a collecting device is ensured. As a result of the special arrangement of the holder for the object carrier above the xy table, which has the effect of a physical separation between the object carrier and the table surface of the xy table, a suitable collecting device can be fed into the free working space which is produced as a result. It is particularly simply possible to bring the collecting device with its at least one container into a position such that parts of the preparation that are cut out pass into the containers provided for the purpose. The user of the device and of the microscope does not need to carry out any complicated handling. The collecting device can be displaced in the free working space on the table surface. This can be done manually or by motor.

A further advantageous feature of the invention is that, as a result of the special arrangement of the object carrier in the holder, the parts of the preparation cut out by the laser beam pass into the containers provided for the purpose on account of the force of gravity. Therefore, no kind of additional action is required, and the risk of contamination or damage to the preparation is virtually ruled out. In order further to avoid contamination of the containers by dust from the ambient air or from parts of preparations which are liberated by the laser cutting, a contamination prevention plate is provided immediately under the holder for the object carrier. The contamination prevention plate is fixed by holding elements to the stationary base plate of the xy table in such a way that an approximately sealed space is produced between the table surface and the contamination prevention plate, under the holder. The contamination prevention plate has an opening which is stationary relative to the optical axis of the objective and through which the light for the preparation illumination passes, and the part of the preparation that is cut out falls into the container.

A further advantage of the invention resides in the fact that the displacement of the preparation is carried out with the existing operating elements of the xy table, which are familiar to the user of conventional microscope tables. In this case, the xy table can be moved both manually and by motor.

Further features and advantages of the invention emerge from the subclaims.

Figure 2:
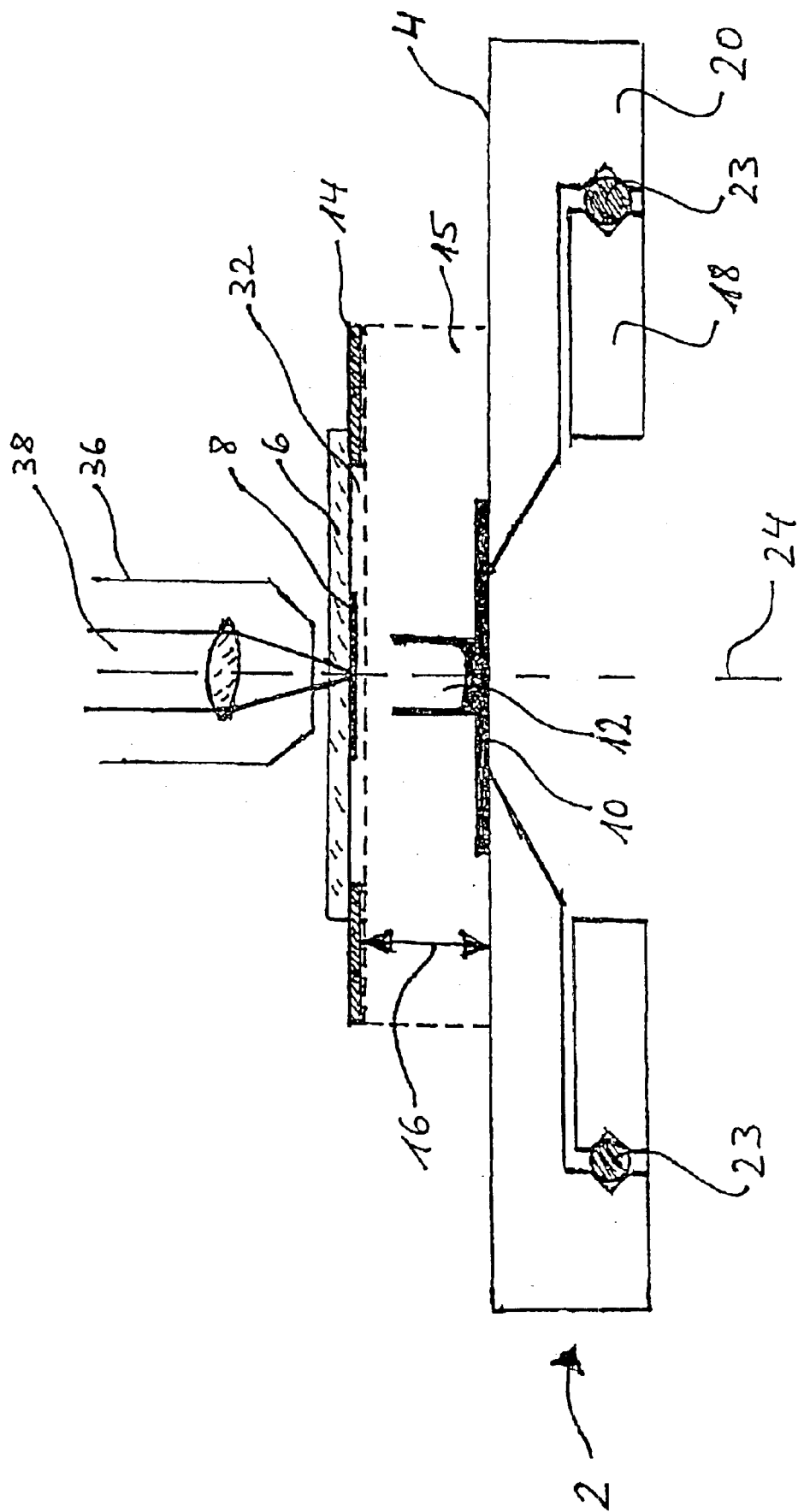
Figure 3:
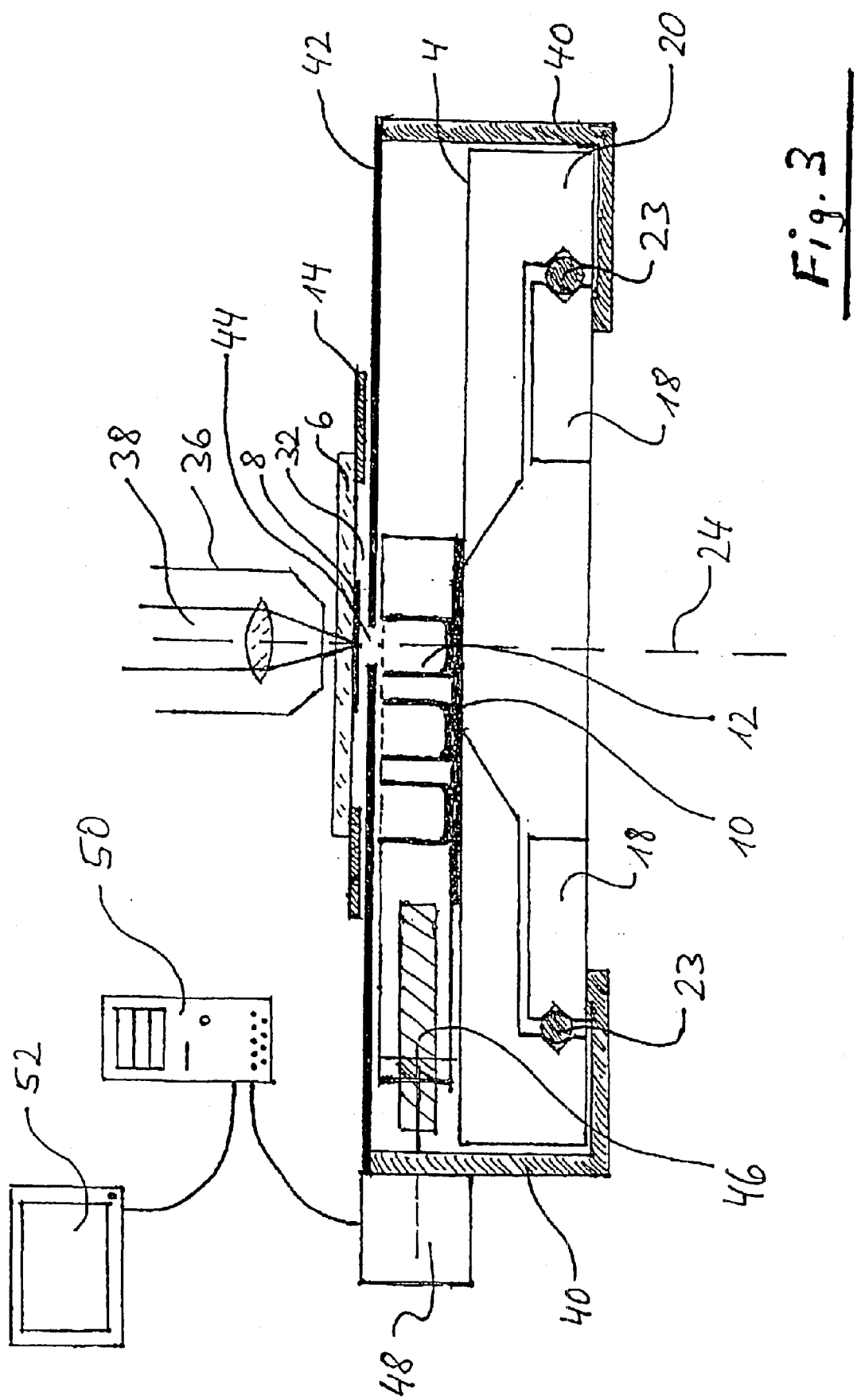

The invention will be described below using the schematic drawing, in which:

FIG. 1 shows a perspective view of the device for holding a preparation for laser cutting FIG. 2 shows a cross section through the device in the plane covered by the optical axis and the x direction, the position of the collecting container additionally being shown, and FIG. 3 shows a second exemplary embodiment of the invention, use being made of the same view as that from FIG. 2.

FIG. 1 shows a device for holding a preparation for laser cutting. The device has an xy table 2, which can be fitted to a conventional microscope (not illustrated). The xy table can be moved manually or by means of motors (not illustrated). The construction of the microscope does not need to be discussed specifically here, since this is sufficiently well known to those skilled in the art. The microscope defines an optical axis 24 which, in FIG. 1, is illustrated as a dashed line.

The xy table 2 has a stationary base plate 18. Fitted to the stationary base plate 18 is a moveable plate 20 which, in the exemplary embodiment illustrated, can be moved in the y direction 20a. In FIG. 1, the y direction 20a is illustrated by a double arrow.

A linear guide 22 which can be moved in the x direction 22a is fitted to the moveable plate 20. The x direction 22a is illustrated in FIG. 1 by a further double arrow. Fixed to the linear guide 22 is a spacer 15, to which a holder 14 for an object carrier 6 is connected. The plate 20 and the linear guide 22 can in each case be moved by means of roller bearings 23. In the exemplary embodiment illustrated, the holder 14 is detachably fixed to the spacer 15 by means of two knurled screws 21.

The xy table 2 defines a table surface 4. The holder 14 is spaced apart from the table surface 4 by the spacer 15 in such a way that a free working space 16 is formed between the table surface 4 and the holder 14.

The xy table 2 has a cutout 26. The cutout 26 is assigned with respect to the microscope in such a way that the optical axis 24 runs through the cutout 26. The holder 14 is configured in a U shape, a first and a second leg 28 and 30 being formed. Between the first and the second leg 28 and 30, a clearance 32 is formed, which is covered by the object carrier 6. The clearance 32 is arranged with respect to the cutout 26 in such a way that the optical axis 24 runs through both. By means of this arrangement of the cutouts 26 in the xy table 2 and of the clearance 32, transmitted light illumination of the preparation 8 applied to the object carrier 6 is possible (see FIG. 2).

FIG. 2 illustrates a cross section through the device from FIG. 1 in the plane covered by the optical axis and the x direction. The plate 20 that can be moved in the y direction is arranged on the stationary base plate 18. The moveable plate 20 defines the table surface 4 of the xy table 2. Provided on the table surface 4 is a collecting device 10, which can be provided with a displacement device (see FIG. 3). It is obvious that the collecting device 10 can also be moved manually in the free working space 16 defined by the spacer 15.

The object carrier 6 is arranged above the clearance 32 in the holder 14 in such a way that the preparation 8 is located completely in the clearance 32. When an object carrier 6 is located on the holder 14, the preparation 8 is arranged in such a way that it is directly opposite the table surface 4. An objective 36 of the microscope is assigned to the object carrier 6 on the optical axis 24, and produces an image of the preparation 8. Furthermore, an injected laser beam 38 is aimed at the preparation 8 by the objective 36, in order to cut a small part out of the preparation 8. The collecting device 10 is located under the preparation 8 in such a way that the part cut out falls directly into a container 12 of the collecting device 10 on account of the force of gravity. The number of containers 12 of the collecting device 10 can be matched to the conditions of use.

FIG. 3 illustrates a further exemplary embodiment of the device for laser cutting preparations 8. Two holding elements 40 are fixed to the stationary base plate 18. The holding elements 40 bear a contamination prevention plate 42 which, between the holder 14 and the collecting device 10, is stationary relative to the optical axis 24. The contamination prevention plate 42 covers the entire table surface 4 and therefore bounds the free working space 16 at the top. It is provided with a cutout 44 around the optical axis 24. The collecting device 10 with containers 12 to hold the preparation elements cut out is arranged in the free working space 16. The collecting device 10 can have an array of containers 12.

The contamination prevention plate 42 prevents dust or other particles from the ambient air being deposited in the containers 12 of the collecting device 10. Added to this is the fact that the contamination prevention plate 42 prevents parts of preparations which are liberated from the preparation 8 during the laser cutting being precipitated into the containers 12. In this case, it proves to be advantageous that, as a result of the cutout 44 in the contamination prevention plate 42, it is always the case that only one container 12 of the collecting device 10 is open, while the remaining containers 12 are covered.

A displacement device 46 is connected to the collecting device 10, and both are arranged on the table surface 4. In addition to manual operation of the displacement device 46, a motor 48 can also be provided to move the displacement device 46 on the table surface 4 by motor.

The motor 48 is connected to a computer 50, which is responsible for the control of the displacement device 46. The computer 50 displaces the collecting device 10 in such a way that in each case the desired container 12 is located under the cutout 44 and therefore under the region of the preparation 8 which is just being subjected to the laser cutting operation. When the laser cutting operation has been completed, the preparation element that has been cut out falls into the container 12 on account of the force of gravity. If required, the computer 50 will position another or an empty container 12 appropriately, in order therewith to catch a new preparation element that has been cut out.

The computer 50 is also connected to a monitor 52. Via the monitor 52, for example with the aid of a mouse (not illustrated), the desired cutting line can be selected by the user and the cutting operation can be observed. In the event that an image analysis system (not illustrated) is installed in the computer 50, the cutting operation can be controlled and monitored. The computer 50 automatically sets the parameters required for an optimum cut automatically [sic], for example intensity of the laser, width of the cutting line, travel speed of the xy table, illumination of the microscope.

The contamination prevention plate 42 is provided directly under the holder 14. The object carrier 6 deposited on the holder 14 can be observed through an objective 34 belonging to the microscope. The objective 34 is fitted, for example, to a turret (not illustrated), in order that a user can choose between several magnifications for viewing the preparations. Likewise provided are optical elements (not illustrated) which inject the laser beam 38 into the microscope in such a way that the laser beam 38 runs substantially along the optical axis 24 of the objective 34. Using one and the same objective 34, an image of the preparation 8 is produced for the user and, at the same time, the laser beam is projected onto the preparation 8 for cutting.

The invention has been described with regard to a specific embodiment, but it is obvious to those skilled in the art that changes and modifications can be made without departing from the area of protection of the following claims in the process.

List of Designations 2 xy table
4 table surface 6 object carrier
8 preparation
10 collecting device
12 container
14 holder
15 spacer
16 free working space
18 stationary base plate
20 plate that can be moved in the y direction
20a y direction
21 knurled screw
22 linear guide
22a x direction
23 roller bearing
24 optical axis
26 cutout
28 first leg
30 second leg
32 clearance
34 objective
38 laser beam
40 holding element
42 contamination prevention plate
44 cutout
46 displacement device
48 motor
50 computer
52 monitor

What is claimed is:

1. Device for laser cutting preparations, comprising an xy table (2) which defines a table surface (4), comprising a holder (14) to hold an object carrier (6), the object carrier (6) being seated in the holder (14) in such a way that the preparation (8) is opposite the table surface (4), and a collecting device (10) having at least one container (12) to collect a part of the preparation cut out, characterized in that the holder (14) is arranged above the table surface (4) and is connected to the xy table (2) in such a way that it can be displaced in the y direction (20a) and in the x direction (22a), and in that, between the holder (14) and the table surface (4), a free working space (16) is defined, into which the collecting device (10) can be fed.

2. The device as claimed in claim 1, characterized in that the xy table (2) has a stationary base plate (18) and a first plate that can be moved in the x direction (22a) and a second plate that can be moved in the y direction, and in that the holder (14) is fixed by at least one spacer (15) to the upper moveable plate.

3. The device as claimed in claim 1, characterized in that the xy table (2) has a stationary base plate (18) and a plate (20) that can be moved in the y direction (20a) and a linear guide (22) that can be moved in the x direction (22a), and in that the holder (14) is fixed by at least one spacer (15) to the linear guide (22).

4. The device as claimed in claim 1, characterized in that the xy table (2) has a stationary base plate (18) and a plate that can be moved in the x direction (22a) and a linear guide that can be moved in the y direction (20a), and in that the holder (14) is fixed by at least one spacer (15) to the linear guide.

5. The device as claimed in claim 2, characterized in that the xy table (2) has motor drives for the x direction (22a) and the y direction (20a).

6. The device as claimed in claim 1, characterized in that a microscope is provided which defines an optical axis (24), in that the xy table (2) has a cutout (26) and is assigned to the microscope in such a way that the cutout (26) is arranged around the optical axis (24), in order to permit transmitted light illumination of the preparation (8).

7. The device as claimed in claim 1, characterized in that the collecting device (10) is connected to a displacement device (46) for positioning the collecting device (10) relative to the preparation (8).

8. The device as claimed in claim 7, characterized in that the displacement device (46) is assigned at least one operating element for manual operation.

9. The device as claimed in claim 7, characterized in that the displacement device (46) is assigned at least one motor (48).

10. The device as claimed in claim 6, characterized in that between the holder (14) and the collecting device (10) there is arranged a contamination prevention plate (42) which is stationary relative to the optical axis (24), is provided with a cutout (44) around the optical axis (24) and which covers the table surface (4).

* * * * *